United States Patent [19]

Baltruschat

[11] Patent Number: 5,674,807
[45] Date of Patent: Oct. 7, 1997

[54] HERBICIDE MIXTURES

[75] Inventor: Helmut Baltruschat, Schweppenhausen, Germany

[73] Assignee: American Cyanamid Company, Parsippany, N.J.

[21] Appl. No.: 406,989

[22] PCT Filed: Oct. 5, 1993

[86] PCT No.: PCT/EP93/02737

§ 371 Date: Aug. 4, 1995

§ 102(e) Date: Aug. 4, 1995

[87] PCT Pub. No.: WO94/07368

PCT Pub. Date: Apr. 14, 1994

[30] Foreign Application Priority Data

Oct. 6, 1992 [EP] European Pat. Off. ............ 92117054

[51] Int. Cl.⁶ .......................... A01N 43/40; A01N 43/48; A01N 43/64; A01N 47/30

[52] U.S. Cl. .......................... 504/130; 504/129; 504/131; 504/132; 504/133; 504/134; 504/135; 504/136; 504/137; 504/138; 504/139; 504/140; 504/141; 504/142; 504/143; 504/144; 504/145; 504/146; 504/147; 504/148; 504/149

[58] Field of Search .................. 504/129, 130, 504/133–137, 131, 132, 138–149; 71/DIG. 1

[56] References Cited

U.S. PATENT DOCUMENTS

| | | | |
|---|---|---|---|
| 4,875,925 | 10/1989 | Hewett et al. | 504/130 |
| 4,929,271 | 5/1990 | Hewett et al. | 504/130 |
| 4,940,484 | 7/1990 | Hewett et al. | 504/130 |
| 4,990,177 | 2/1991 | Hewett et al. | 504/130 |
| 5,013,353 | 5/1991 | Hewett et al. | 504/130 |
| 5,264,411 | 11/1993 | Hewett et al. | 504/130 |
| 5,384,305 | 1/1995 | Foster et al. | 504/130 |

FOREIGN PATENT DOCUMENTS

| | | |
|---|---|---|
| 0 223 449 | 5/1987 | European Pat. Off. |
| 0 257 771 | 3/1988 | European Pat. Off. |
| 0 274 892 | 7/1988 | European Pat. Off. |
| 0 447 004 A2 | 9/1991 | European Pat. Off. |
| 2 611 437 | 9/1988 | France. |

*Primary Examiner*—John Pak
*Attorney, Agent, or Firm*—Gregory M. Hill

[57] ABSTRACT

The efficacy of defined aryloxypicolinamide herbicides, in particular their spectrum of weed control and selectivity for the crop species, is synergistically enhanced by combination with one or more selected second herbicidal compounds.

24 Claims, No Drawings

HERBICIDE MIXTURES

This application is a 371 of PCT/EP93/02737, filed on Oct. 5, 1993.

The present invention relates to an improvement in the efficacy of aryloxypicolinamide herbicides by combination with a selected second herbicidal compound.

Aryloxypicolinamides are a novel group of compounds, claimed in Applicants' European Patent No. 447004, which show excellent herbicidal activity, in particular against broad leaf weeds in cereal crops. However, the aryloxypicolinamides when used as the sole active ingredient do not always achieve effective control of the full spectrum of weed species encountered in commercial agronomic practice, in conjunction with reliable selectivity for the crop species. Such gaps in the spectrum of control can often be remedied by co-treatment with another herbicide known to be effective against the relevant weed species. In the course of their investigations into the efficacy of various partners for aryloxypicolinamides, Applicants have found that selected combinations produce not merely the expected, additive effect, but exhibit a significant synergistic effect (i.e. these combinations show a much higher level of activity than predicted from that of the individual compounds) which enables a greater selectivity for the crop species.

A mixture of herbicides shows a synergistic effect if the herbicidal activity of the mixture is larger than sum of activities of the separately applied compounds. The expected herbicidal activity for a given mixture of two herbicides can be calculated as follows: (comp. Colby, S. R., "Calculating synergistic and antagonistic response of herbicide combinations", Weeds 15, pp 20–22 (1967)):

$$WE. = X + \frac{Yx(100 - X)}{100}$$

Wherein

X is the percentage of growth inhibition upon treatment with a herbicide 1 at a dosage of p kg/ha compared with an untreated control (X=0%)

Y is the percentage of growth inhibition upon treatment with a herbicide 2 at a dosage of q kg/ha compared with an untreated control WE. is the herbicidal effect to be expected upon treatment (% of growth inhibition compared with untreated control) with a combination of herbicide 1 and 2 at a dosage of p+q g/ha If the actual weed control (W) exceeds the expected (calculated) weed control (WE), the mixture shows a synergistic effect.

Thus, the combinations of the present invention not only achieve control of certain weed species which are difficult to combat effectively with aryloxypicolinamides alone, in particular grass weeds such as *Alopecurus myosuroides; Apera spica-venti*; and *Echinocloa crus-galli*, but also show significant synergistic increase in the level of activity against those weeds and also many broad-leaved weeds. This combination of advantages yields important benefits in practical agronomic applications. Firstly, it provides treatment for cereal crops which will control the majority of the significant weed species; secondly it enables that effective control to be attained with lower application rates of active material—with consequential environmental benefits and also greater selectivity of action in favour of the crop species.

Accordingly, the present invention provides a herbicidal composition comprising a herbicidally acceptable carrier and/or surface active agent together with, as active ingredient, a mixture of:

at least one aryloxypicolinamide of the general formula I

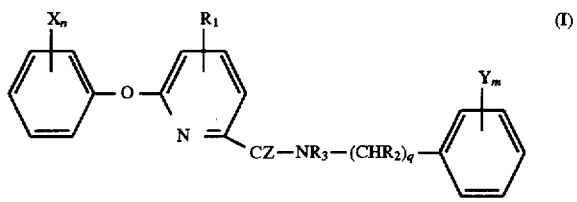

in which

Z represents an oxygen or sulphur atom;

$R_1$ represents a hydrogen or halogen atom or an alkyl or haloalkyl group;

$R_2$ represents a hydrogen atom or an alkyl group; q is 0 or 1;

$R_3$ represents a hydrogen atom or an alkyl or alkenyl group;

the or each group X independently represents a halogen atom or an optionally substituted alkyl or alkoxy group, preferably a haloalkyl group, or an alkenyloxy, cyano, carboxy, alkoxycarbonyl, (alkylthio)carbonyl, alkylcarbonyl, amido, alkylamido, nitro, alkylthio, haloalkylthio, alkenylthio, alkynylthio, alkylsulphinyl, alkylsulphonyl, alkyloximinoalkyl or alkenyloximinoalkyl group;

n is 0 or an integer from 1 to 5;

the or each group Y independently represents a halogen atom or an alkyl, nitro, cyano, haloalkyl, alkoxy or haloalkoxy group;

and m is 0 or an integer from 1 to 5;

together with a second herbicidal component selected from:

a) a urea-type herbicide, in particular chlortoluron, isoproturon, linuron or neburon;

b) a triazine-type herbicide in particular atrazine, cyanazine or simazine;

c) a hydroxybenzonitrile herbicide in particular bromoxynil or ioxynil; and d) an aryloxyalkanoic acid herbicide in particular dichlorprop, diclofop, MCPA or mecoprop (CMPP).

e) a dinitroaniline herbicide, such as pendimethalin;

f) a thiocarbamate herbicide, such as prosulfocarb;

g) amidosulfuron;

h) a diphenyl ether herbicide, such as aclonifen;

i) a pyridazine herbicide, such as pyridate;

j) a fluorene carboxylic acid herbicide, such as flurenol;

k) a pyridyloxyacetic acid herbicide, such as fluroxypyr;

l) an arylalanine herbicide, such as flamprop-isopropyl.

The pattern of persistence of the aryloxypicolinamide (abbreviated herein as "AOP") is such that the combined treatment of the present invention can be attained either by the application of a prepared mixture as defined above, or by time separated application of separate formulations. Hence, in another embodiment, the present invention provides a method for controlling the growth of weeds at a cereal crop locus which comprises applying to the locus an AOP as defined in above, and a second component which is selected from those listed above.

The treatment according to the invention may be used to control a broad spectrum of weed species in cereal crops, e.g. wheat, barley, rice and maize by pre- or postemergence treatment, especially early and late post-emergence, without significant damage to the crop.

The term "pre-emergence application" means application to a soil in which seeds or seedlings are present before the emergence of the weeds above the surface of the soil. "Post-emergence application" means application to the aerial or exposed portions of the weeds which have emerged above the surface of the soil.

Weeds that may be controlled by the combinations include:

| | | |
|---|---|---|
| Veronica persica | Veronica hedearaefolia | Stellaria media |
| Lamium purpureum | Lamium amplexicaule | Aphanes arvensis |
| Galium aparine | Alopecurus myosuroides | Matricaria inodora |
| Matricarria matricoides | Anthemis arvensis | Papaver rhoeas |
| Poa annua | Apera spica-venti | Phalaris paradoxa |
| Phalaris minor | Avena fatua | Lolium perenne |
| Bromus sterilis | Poa trivialis | Spergula arvensis |
| Cerastes holosteoides | Arenaria seryllifolia | Silene vulgaris |
| Legousia hybrida | Geranium dissectum | Montia perfoliata |
| Myosotis arvensis | Chenopodium arvensis | Polygonum aviculare |
| Polygonum lapathifolium | Polygonum convolvulus | |
| Chrysantemum segetum | Centaurea cyanus | Galeopsis tetrahit |
| Senecio vulgaris | Cirsium arvense | Viola arvensis |

An exemplary compound for use as the aryloxypicolinamide component is of the general formula:

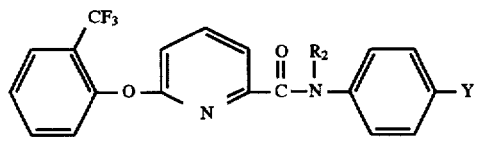

(II)

wherein $R_2$ is a hydrogen atom or an ethyl group, and Y is a hydrogen or fluorine atom.

The application rate of the AOP component is normally in the range of 25 to 250 grams of active ingredient (gai) per hectare, with rates between 30–100 gai/ha often achieving satisfactory control and selectivity. The optimal rate for a specific application will depend on the crop(s) under cultivation and the predominant species of infesting weed and can readily be determined by established biological tests.

The selection of the second component will likewise be dependent on the crop/weed situation to be treated, and will be readily identifiable by those skilled in this area. The application rate of the second component is determined primarily by the chemical type of that component, since the intrinsic activity of different types of herbicide varies widely. For example, the activity of a triazine herbicide, such as cyanazine or simazine, can be almost tenfold greater than that of a urea herbicide such as chlortoluron or isoproturon. In general, the application rate of the second component is in the range of 500 to 5000 gai/ha, preferably 1000–2500 gai/ha, when the second component is a urea or thiocarbamate herbicide; in the range 25 to 100 gai/ha when the second component is amidosulfuron or a pyridyloxyacetic acid herbicide; and in the range 100 to 750 gai/ha when the second component is one of the other herbicide groups listed above. Again, the optimal rate for the chosen second component will depend on the crop(s) under cultivation and the level of weed infestation, and can readily be determined by established biological tests. Naturally, with such a wide variation in application rate for the second component, the ratio of AOP to that second component will be determined predominantly by the choice of second component. Thus, the ratio AOP: Second Component may vary from 2:1 (second component=amidosulfuron) to 1:60 (second component=prosulfocarb).

I claim:

1. Herbicidal composition comprising a herbicidally acceptable carrier and/or surface active agent together with, as active ingredient, a herbicidally effective amount of a mixture of at least one aryloxypicolinamide (AOP) compound of the formula

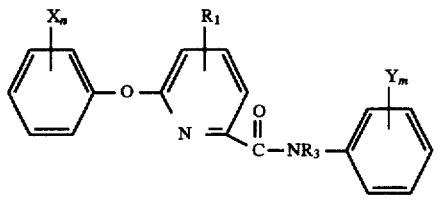

in which $R_1$ represents a hydrogen or halogen atom or an alkyl or haloalkyl group;

$R_3$ represents a hydrogen atom or an alkyl or alkenyl group;

each X independently represents a halogen atom or an optionally substituted alkyl or alkoxy group, or an alkenyloxy, alkynyloxy, cyano, carboxy, alkoxycarbonyl, (alkylthio)carbonyl, alkylcarbonyl, amido, alkylamido, or nitro group;

n is 0 or an integer from 1 to 5;

each Y independently represents a halogen atom or an alkyl, nitro, cyano, haloalkyl, alkoxy or haloalkoxy group; and m is 0 or an integer from 1 to 5; together with a second component selected from the group consisting of:

(a) a urea herbicide;

(b) a triazine herbicide;

(c) a hydroxybenzonitrile herbicide;

(d) an aryloxyalkanoic acid herbicide;

(e) a dinitroaniline herbicide;

(f) a thiocarbamate herbicide;

(g) amidosulfuron;

(h) a diphenyl ether herbicide;

(i) a pyridazine herbicide;

(j) a fluorene carboxylic acid herbicide;

(k) a pyridyloxyacetic acid herbicide; and (l) an arylalanine herbicide wherein the weight ratio of AOP to said second component in said composition ranges from 2:1 to 1:60.

2. Composition as claimed in claim 1 wherein the second component is selected from the group consisting of chlortoluron, isoproturon, cyanazine, bromoxynil, ioxynil, dichloroprop, diclofop, MCPA, mecoprop (CMPP), pendimethalin, prosulfocarb, amidosulfuron, aclonifen, pyridate, flurenol, fluroxypyr, and flamprop-isopropyl.

3. Composition as claimed in claim 1 wherein said second component is a urea or thiocarbamate herbicide and the ratio of AOP to said second component is 1:10 to 1:60.

4. Composition as claimed in claim 1 wherein said second component is amidosulfuron or a pyridyloxyacetic acid and the ratio of AOP to said second component is 2:1 to 1:20.

5. Composition as claimed in claim 1 wherein said AOP compound has the formula:

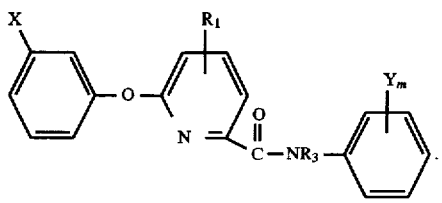

6. Composition as claimed in claim 1 wherein X is haloalkyl.

7. Composition as claimed in claim 5 wherein X is haloalkyl.

8. Composition as claimed in claim 7 wherein X is $CF_3$.

9. Method of controlling the growth of weeds at a cereal locus which comprises applying to the locus an effective amount of the herbicidal composition of claim 1.

10. Method as claimed in claim 9 wherein the AOP is applied to the locus at a rate of 25 to 250 gai/ha.

11. Method as claimed in claim 9 wherein the second component is a urea or thiocarbamate herbicide and is applied to the locus at the rate of 1000–2500 gai/ha.

12. Method as claimed in claim 9 wherein the second component is amidosulfuron or a pyridyloxyacetic acid herbicide and is applied to the locus at the rate of 25 to 100 gai/ha.

13. Method as claimed in claim 9 wherein said AOP compound is

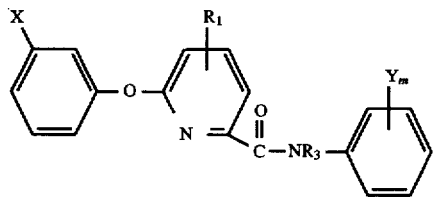

where X is haloalkyl.

14. Method as claimed in claim 13 wherein X is $CF_3$.

15. A herbicidal composition comprising a herbicidally acceptable carrier and/or surface active agent together with, as active ingredient, a herbicidally effective amount of a mixture of at least one aryloxypicolinamide (AOP) compound of formula:

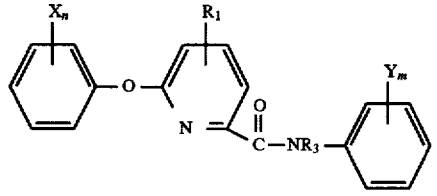

wherein $R^3$ represents a hydrogen atom or an alkyl group;
X represents a haloalkyl group;
$R_1$ represents a hydrogen or halogen atom or an alkyl or haloalkyl group;
Y represents a halogen atom; and
m is 0 to 1;
together with a second component selected from the group consisting of chlortoluron, isoproturon, cyanazine, bromoxynil, ioxynil, dichlorprop, diclofop, MCPA, mecoprop (CMPP), pendimethalin, prosulfocarb, amidosulfuron, aclonifen, pyridate, flurenol, fluroxypyr and flamprop-isopropyl, wherein the weight ratio of AOP to the second component is 2:1 to 1:60.

16. Composition as claimed in claim 15, wherein the weight ratio of AOP to said second component is from 1:2 to 1:60.

17. Composition as claimed in claim 15, wherein the weight ratio of AOP to said second embodiment is from 1:10 to 1:60.

18. Composition as claimed in claim 15 wherein said AOP compound has the formula:

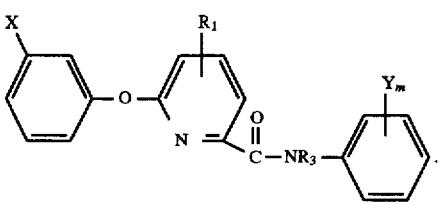

19. Composition as claimed in claim 15 wherein X is haloalkyl.

20. Composition as claimed in claim 18 wherein X is haloalkyl.

21. Composition as claimed in claim 20 wherein X is $CF_3$.

22. Method of controlling the growth of weeds at a cereal locus which comprises applying to the locus an effective amount of the herbicidal composition of claim 15.

23. Method as claimed in claim 22 wherein said AOP compound is

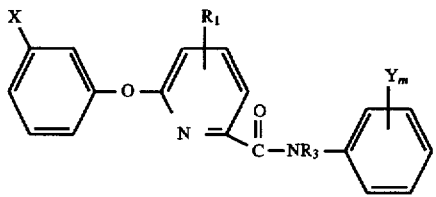

where X is haloalkyl.

24. Method as claimed in claim 23 where X is $CF_3$.

* * * * *